United States Patent
Zheng et al.

(10) Patent No.: US 12,029,860 B1
(45) Date of Patent: Jul. 9, 2024

(54) MOTION SICKNESS PREVENTION WRISTBAND AND A CONTROL METHOD THEREOF

(71) Applicants: Hao Zheng, Zhejiang (CN); Ningning Gui, Zhejiang (CN); Sen Li, Zhejiang (CN); Kai Lu, Zhejiang (CN); Zhouming Zhu, Zhejiang (CN)

(72) Inventors: Hao Zheng, Zhejiang (CN); Ningning Gui, Zhejiang (CN); Sen Li, Zhejiang (CN); Kai Lu, Zhejiang (CN); Zhouming Zhu, Zhejiang (CN)

(73) Assignee: NINGBO KANGLUO INTELLIGENT TECHNOLOGY CO., LTD, Ningbo (CN)

( * ) Notice: Subject to any disclaimer, the term of this patent is extended or adjusted under 35 U.S.C. 154(b) by 0 days.

(21) Appl. No.: 18/236,918

(22) Filed: Aug. 22, 2023

(51) Int. Cl.
*A61M 21/00* (2006.01)
*A61N 1/04* (2006.01)
*A61N 1/36* (2006.01)

(52) U.S. Cl.
CPC .......... *A61M 21/00* (2013.01); *A61N 1/0472* (2013.01); *A61N 1/36025* (2013.01); *A61M 2021/0066* (2013.01); *A61M 2021/0072* (2013.01); *A61M 2205/07* (2013.01); *A61M 2205/3344* (2013.01); *A61M 2205/3368* (2013.01); *A61M 2205/3379* (2013.01); *A61M 2205/502* (2013.01); *A61M 2209/088* (2013.01)

(58) Field of Classification Search
None
See application file for complete search history.

(56) References Cited

U.S. PATENT DOCUMENTS

| | | | | |
|---|---|---|---|---|
| 10,849,822 | B2 * | 12/2020 | Zhang | A61N 1/36 |
| 11,478,606 | B1 * | 10/2022 | English | A61M 21/02 |
| 2018/0110960 | A1 * | 4/2018 | Youngblood | A47C 21/048 |
| 2021/0283400 | A1 * | 9/2021 | Hamner | A61N 1/36178 |

OTHER PUBLICATIONS

[In-Depth Look] The Parts and Pieces That Make the Gear S3 tick.—Samsung Global Newsroom. (Nov. 14, 2016). https://news.samsung.com/global/in-depth-look-the-parts-and-pieces-that-make-the-gear-s3-tick (Year: 2016).*

* cited by examiner

*Primary Examiner* — Christine H Matthews
*Assistant Examiner* — Marc D. Honrath
(74) *Attorney, Agent, or Firm* — Jeenam Park (57) ABSTRACT

The present invention discloses a motion sickness prevention wristband and a control method thereof, wherein the motion sickness prevention wristband comprises wristband body, and further comprises microcontroller unit MCU, pressure sensor, electrode assembly, and air bag control assembly; pressure sensor, electrode assembly, and air bag control assembly are electrically connected to the MCU, and air bag control assembly is resisted against electrode assembly; pressure sensor, for obtaining contact pressure value between electrode assembly and the surface of the human skin; the MCU, for determining air pressure control data; and air bag control assembly, control air pressure change to enable the MCU to apply electrical stimulation to electrode assembly after the air pressure change. The air pressure change enables electrode assembly to better adhere to the skin, the electrical stimulation performed can maintain contact resistance, keep the electrical stimulation, thereby significantly enhancing the effect of anti-motion sickness.

19 Claims, 9 Drawing Sheets

MOTION SICKNESS PREVENTION WRISTBAND AND A CONTROL METHOD THEREOF

TECHNICAL FIELD

The present invention relates to the technical field of intelligent wearable, in particular to a motion sickness prevention wristband and a control method thereof.

BACKGROUND

Motion sickness, is an illness that occurs when any form of accelerated motion, such as the jolts, swings, or rotations produced by the motion of a car, ship, or airplane, stimulates the vestibular nerves of the human body. When motion sickness occurs, the person experiences a great deal of discomfort and psychological fear of motion sickness.

Currently on the market for the relief of motion sickness, seasickness, airsickness and other symptoms of the main corresponding drugs, is not suitable for long-term use, and other anti-motion sickness products have aromatic gas also stimulate the acupoints of the product, in general there is a lack of effect is not obvious, not easy to wear and other shortcomings.

To further alleviate the discomfort caused by motion sickness, while avoiding drug abuse, U.S. patent Ser. No. 10/849,822 discloses a therapeutically stable antiemetic control device and control method, which simulates the bioelectrical physiological signals, periodically releases weak electrical energy to generate electrical stimulation, and the excitatory electrical signals generated by the electrical stimulation reach the vestibular center through the nerves to compensate or attenuate the excessive bioelectrical power generated in the vestibule due to excessive human movement, and the transmission of vestibular nerve impulses to the central center is reduced or inhibited, thereby increasing the tolerance of the vestibular organs to various motor stimuli and normalizing gastric motility.

One form of implementation of this solution is a motion sickness prevention wristband, which is provided with an electrode piece near the median nerve and is fastened by a wristband so that the electrode piece is tightened against the skin of the wrist. However, this embodiment still suffers from the following problems: first, the wristband attachment is uncomfortable to wear and affects blood circulation; second, the contact force of electrode piece with the skin and the contact resistance is uncontrollable, which affects the effectiveness of stimulation; third, the surface of the electrode piece is dry, which also affects the effectiveness of stimulation.

Based on the above problems, it is necessary to propose a new motion sickness prevention wristband, which wristband can significantly improve the effect of anti-motion sickness, and at the same time, it is convenient to wear and use, and has better practicality.

SUMMARY

The present invention provides a motion sickness prevention wristband comprising wristband body, microcontroller unit (MCU), pressure sensor, electrode assembly, and air bag control assembly, wherein pressure sensor, electrode assembly, and air bag control assembly are electrically connected to the MCU; air bag control assembly is offset from electrode assembly; pressure sensor is used to obtain contact pressure value between electrode assembly and the surface of human skin and transmit contact pressure value to the MCU; the MCU determines air pressure control data for air bag control assembly based on contact pressure value and transmits air pressure control data to air bag control assembly; and air bag control assembly performs an air pressure change so that the MCU applies electrical stimulation to electrode assembly after the air pressure change.

The present invention also provides a method of controlling a motion sickness prevention wristband, the method comprising:

providing a motion sickness prevention wristband that includes wristband body, a microcontroller unit (MCU), pressure sensor, electrode assembly, and air bag control assembly, wherein pressure sensor, electrode assembly, and air bag control assembly are electrically connected to the MCU; air bag control assembly is offset from electrode assembly; pressure sensor is used to obtain a contact pressure value between electrode assembly and the surface of human skin and transmit the contact pressure value to the MCU; the MCU determines an air pressure control data targeting air bag control assembly based on the contact pressure value and transmits the air pressure control data to air bag control assembly; air bag control assembly makes the air pressure change to cause the MCU to apply electrical stimulation to electrode assembly after the air pressure change;

The control method includes obtaining contact pressure value between electrode assembly of motion sickness prevention wristband and the surface of human skin; determining air pressure control data for air bag control assembly of motion sickness prevention wristband based on contact pressure value; and applying electrical stimulation to electrode assembly after the air pressure change in case air bag control assembly performs the air pressure change based on air pressure control data.

BRIEF DESCRIPTION OF DRAWINGS

In order to explain the technical scheme of this application more clearly, the drawings needed in the implementation will be briefly introduced below. Obviously, the drawings described below are only some implementations of this application. For those skilled in the art, other drawings can be obtained according to these drawings without creative work.

DESCRIPTION OF EMBODIMENTS

While various aspects and features of certain embodiments have been summarized above, the following detailed description illustrates a few exemplary embodiments in further detail to enable one skilled in the art to practice such embodiments. Reference will now be made in detail to embodiments of the inventive concept, examples of which are illustrated in the accompanying drawings. The accompanying drawings are not necessarily drawn to scale. The described examples are provided for illustrative purposes and are not intended to limit the scope of the invention. It should be understood, however, that persons having ordinary skill in the art may practice the inventive concept without these specific details.

It will be understood that, although the terms first, second, etc. may be used herein to describe various elements, these elements should not be limited by these terms. These terms are only used to distinguish one element from another. For example, a first attachment could be termed a second attachment, and, similarly, a second attachment could be termed a first attachment, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items. As used in the description of the inventive concept and the appended claims, the singular forms "a," "an," and "the" are intended to include the plural forms as well, unless the context clearly indicates other.

In describing the preferred embodiments, specific terminology will be resorted to for the sake of clarity. It is to be understood that each specific term includes all technical equivalents which operate in a similar manner to accomplish a similar purpose.

The present invention relates to a motion sickness prevention wristband and a control method thereof for relieving symptoms such as motion sickness, seasickness and airsickness. In background technology, the main means for preventing motion sickness is medication, but medication has side effects and dependence and is not suitable for long-term use. There are also anti-motion sickness products based on aromatic gases or stimulation of acupoints, but the effect of these products is unstable and they are not easy to carry and use.

To overcome the above drawbacks, an anti-motion sickness scheme based on electrical stimulation of the median nerve (Neiguan acupoint) is also proposed in the background art, which can achieve the effect of stopping vomiting by low frequency stimulation. One embodiment of this scheme is in the form of a motion sickness prevention wristband, which wristband is provided with an electrode piece near the median nerve and is fastened by a wristband so that the electrode piece is tightened against the skin of the wrist. However, this embodiment still suffers from the following problems: first, the wristband attachment is uncomfortable to wear and affects blood circulation; second, the contact force between electrode piece and the skin and the contact resistance are uncontrollable, affecting the effectiveness of stimulation; and third, the surface of the electrode piece is dry, which also affects the effectiveness of stimulation.

In response to the above problems, the present invention provides a motion sickness prevention wristband and a control method thereof for realizing better fit to electrical stimulation based on changes in air pressure, wherein the wristband can automatically adjust the contact force between the electrode piece and the skin and the contact resistance according to the changes in air pressure, so as to improve the effectiveness of the stimulation. The motion sickness prevention wristband of the present invention has the following advantages: first, it significantly improves the motion sickness prevention effect; second, it is convenient to carry and use; and third, it has better practicality.

Figure 1:
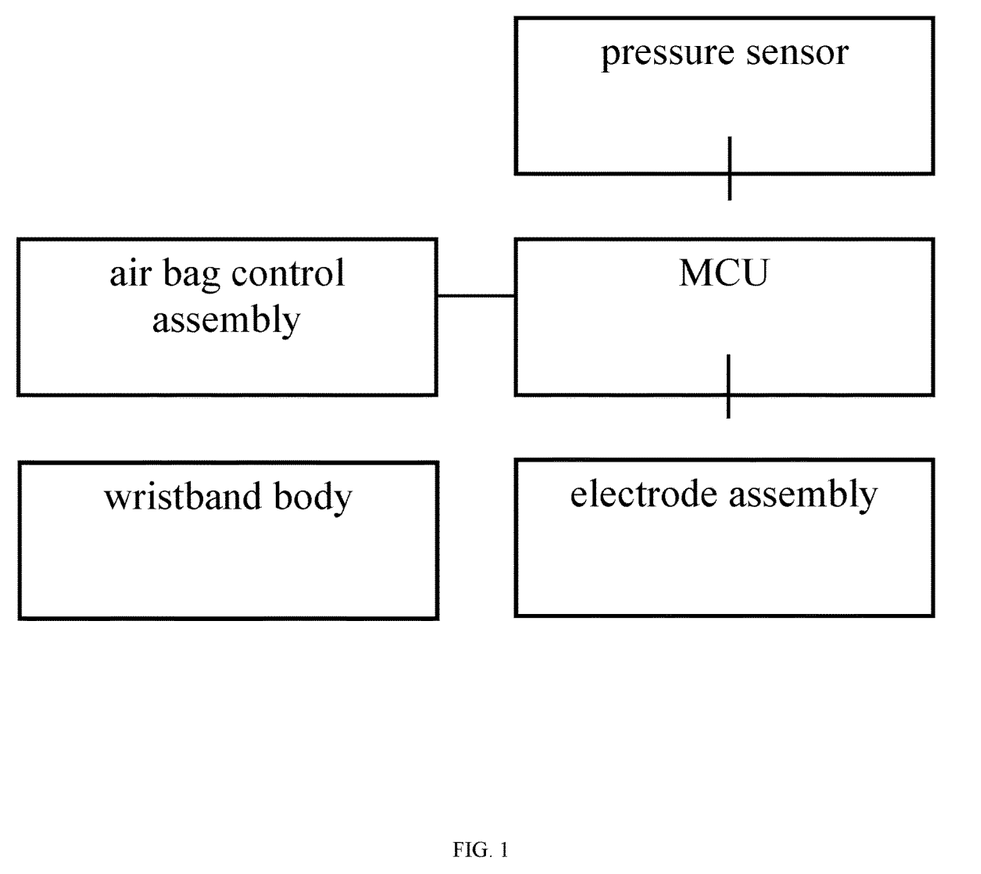
FIG. 1 is a schematic diagram of the blocks of the invention.

As shown in FIG. 1, the motion sickness prevention wristband includes a wristband body, a microcontroller unit (MCU), a pressure sensor, an electrode assembly, and air bag control assembly, wherein the pressure sensor, the electrode assembly, and the air bag control assembly are electrically connected to the MCU, and the air bag control assembly is offset against the electrode assembly, and the pressure sensor is used to obtain a contact pressure value between the electrode assembly and the surface of the human skin, and transmit the contact pressure value to the MCU, which determines air pressure control data targeting the air bag control assembly based on the contact pressure value, and transmits the air pressure control data to the air bag control assembly, which is used to make a change in the air pressure based on the air pressure control data to cause the MCU to apply electrical stimulation to electrode assembly after the air pressure change.

The present invention provides a control scheme for motion sickness prevention wristband that can be realized by the electrically connected relationship of microcontroller unit (MCU) with components such as pressure sensor, electrode assembly and air bag control assembly. Wherein the pressure sensor can obtain a contact pressure value between the electrode assembly and the surface of the human skin in real time or non-real time (e.g., timed), wherein the larger the value of this pressure, to a certain extent, indicates that electrode assembly is more tightly adhered to the human skin, which makes the effectiveness of applying electrical stimulation to the electrode assembly relatively good, and vice versa the smaller the value of the pressure, which to a certain extent, indicates that the electrode assembly is more loosely adhered to the human skin, which makes the effectiveness of applying electrical stimulation to the electrode assembly relatively poor.

In order to avoid as much as possible the problem of poor effectiveness of electrical stimulation brought about by the wristband and human skin not fitting tightly, the present invention has an air bag control assembly under the electrode assembly, and in the case that the contact pressure value measured by the MCU through the pressure sensor is not large enough, air pressure control can be carried out for air bag control assembly to make electrode assembly fit better to human skin after air pressure change, and contact pressure can be increased, at which time electric stimulation is performed to better alleviate symptoms such as motion sickness, and the effect of preventing motion sickness is stronger. and other symptoms, and the effect of preventing motion sickness is stronger.

In this embodiment, the electrode assembly may be a single electrode piece or a plurality of electrode pieces (e.g., an electrode group formed by two electrode pieces), and the MCU may determine air pressure control data for the air bag control assembly based on the contact pressure value between electrode piece and the human skin to control the air pressure change of the air bag control assembly.

The air pressure control data is mainly the control data related to making the air pressure change of the air bag control assembly, for example, in the case where the air bag control assembly includes an air bag, the control data may be the inflation amount of the air bag, realizing the control of the contact strength of the air bag with the skin, and thereby controlling the contact strength of electrode assembly with the human skin, and in the case where it is determined that the air pressure change generated by the air bag control assembly makes the contact pressure sufficiently large, the MCU may apply electrical stimulation to the electrode assembly.

On the one hand, the air bag control assembly holds the electrode tightly against the concave surface of the skin, and compared to the ring-shaped solution that relies solely on the wristband for fastening, the wristband does not need to be tightened for wearing, and wearing the wristband loosely still ensures that the electrode is held tightly against the skin and maintains a stable contact resistance, which also ensures comfort of use under the premise of ensuring the effectiveness of the electrical stimulation.

On the other hand, the air bag control assembly pushes the electrode up into the recessed skin, making the electrode physically closer to the median nerve deep in the wrist, improving the efficiency of electric field propagation in the organism, and making it easier for electric stimulation of the same power to produce better stimulation effects.

Since the air bag control assembly plays a key role in the motion sickness prevention wristband provided by the present invention, it will be highlighted first below.

In this embodiment, there are two ways of fitting air bag control assembly: one is using the motorized fitting of electric air pump with air bag, and the other is using the manual fitting of the manual inflation and deflation unit with the air bag.

When combining electric air pump and air bag for cooperating work, electric air pump, through the electrical connection relationship with the MCU (see FIG. 2), electric air pump can receive the air pressure control data transmitted from the MCU and can determine the inflation and deflation volume required by the air bag based on it. In practice, the electric air pump can be connected to the air bag through a conduit, and the electric air pump can quickly pump and bleed air into the air bag when working. In addition, the electric air pump can adjust the gas pressure inside the air bag according to different electrical stimulation modes on a curve basis, i.e., continuous and smooth pressure control of the air bag can be realized by electric air pump in case the MCU determines the corresponding electrical stimulation mode.

In order to better realize the air pressure control for air bag, the embodiment of the present invention may also set up air pressure sensor inside the air bag, capable of detecting an air pressure sensor inside the air bag in real time, and the MCU, in accordance with this air pressure sensor as well as the contact pressure value obtained from the measurement of pressure sensor, may determine the air pressure control data adapted to electric air pump.

Figure 2:
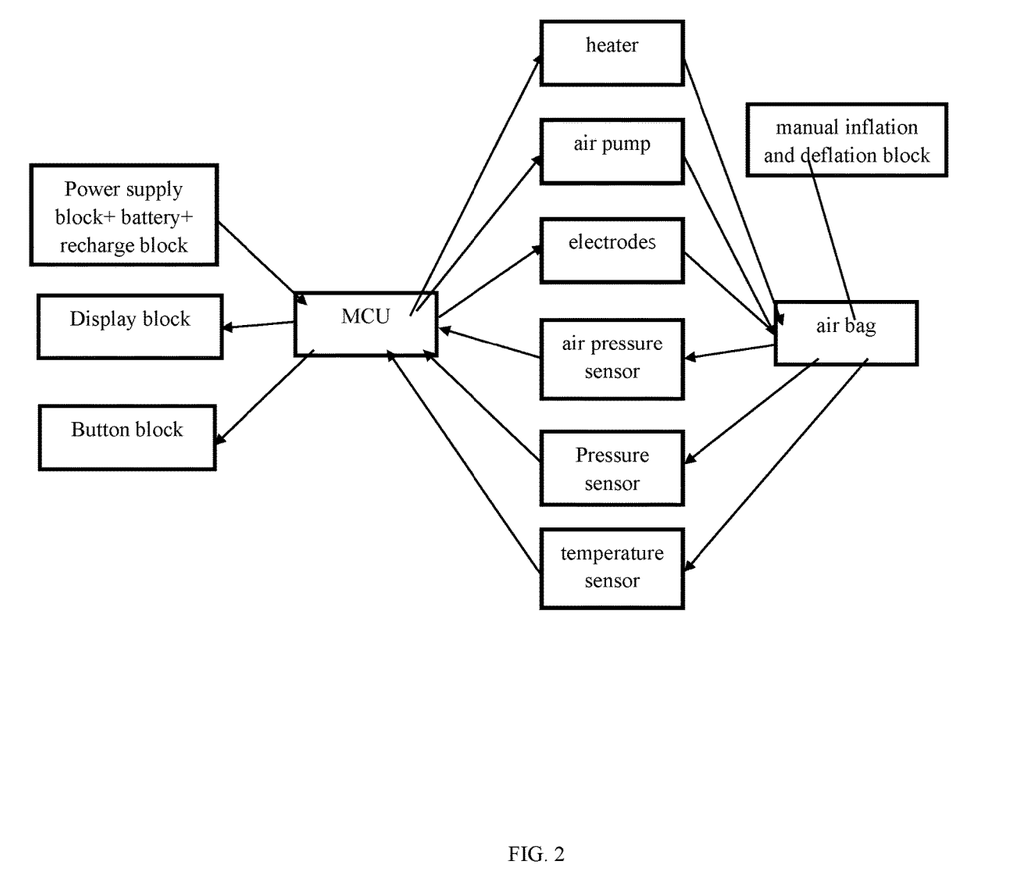
FIG. 2 is a schematic diagram of another block of the present invention.

When the manual inflation and deflation unit and the air bag are combined to work together, as shown in FIG. 2, the manual inflation and deflation module (i.e., manual inflation and deflation unit) includes an inflation port, which can be connected to the hand cupping air pump to support manually pumping gas into air bag, and one-way air valve set in manual inflation and deflation unit makes the gas manually pumped into air bag stay inside air bag, and one-key deflation button is deflated by turning on one-way air valve, which means that the gas valve is briefly shifted when the button is pressed, and the gas valve has the ability to pass gas in the reverse direction, thus realizing rapid deflation. The valve has the ability to vent in the reverse direction, thus realizing rapid deflation.

The main reason why one-key deflation button is used here to realize rapid deflation is to prevent the situation where air bag cannot be deflated automatically if the electric air pump fails. In some embodiments, when the electric air pump is not loaded, manual inflation and deflation unit can also be matched with air bag to independently accomplish the function of jacking up electrode assembly.

In other embodiments, a semi-automatic and semi-manual control method can also be used, for example, when air bag is in a relatively deflated state, the manual control method can be utilized to quickly inflate air bag, and when the specific electrical stimulation is performed, the final inflation effect can be determined based on a precise automatic control method. In practical application, this can be determined by combining the different needs of different users, and no specific limitations are made herein.

Either way, the motion sickness prevention wristband provided by the embodiment of the present invention is capable of non-invasively tipping the electrode at the front end of the air bag into the skin through the expansion of the air bag.

Also as shown in FIG. 2, the MCU, through its electrically connected relationship with pressure sensor, can also read the contact pressure value of the contact surface between air bag and the skin (which corresponds to the contact pressure between electrode assembly and the skin), and modulate air pump to realize the control of the strength of the contact between air bag and the skin, and thus control the strength of the contact between electrode and the skin.

In some embodiments, reminder assembly is also provided so that the user can be prompted to adjust the looseness or tightness of wristband when the contact strength is too large or too small, which is mainly in consideration of the fact that too small a pressure is likely to lead to insufficient contact force between electrode and the skin, resulting in electrode contact resistance becoming large, electrical stimulation effectiveness being reduced, and the skin heating being increased, and too large a pressure is likely to lead to patient discomfort.

In some embodiments, the MCU may analyze and regulate the air pump work strategy based on the data recorded by pressure sensor. For example, lowering the air pump power when the pressure is too high, and then, for example, driving the air pump to work when the pressure is too low. If the pressure is still too low when the air pump is in a high power working state, for example, if it is determined that the updated contact pressure value between the electrode assembly and the surface of the human skin after a change in the air pressure is less than the preset pressure value, reminder signal for reminding the user to tighten the wearing of the wristband may be generated and the user may be prompted by display screen that the wearing of the wrist strap needs to be tightened.

Considering that the process of electrical stimulation will lead to local tissue warming, and too high a temperature may cause discomfort or injury to the user, it is necessary to combine temperature sensor with a temperature measurement in order to set a safe temperature wall for electrical stimulation.

As shown in FIG. 2, the present invention provides motion sickness prevention wristband in which temperature sensor is also included, and temperature sensor is electrically connected to the MCU, which can detect temperature value between electrode assembly and the surface of human skin in order for the MCU to determine electrical stimulation strategy against electrode assembly based on temperature value.

In some embodiments, the temperature sensor in question may be provided outside of air bag, e.g., provided in the vicinity of electrode assembly to determine electrode heating, and if the temperature measured by the temperature sensor reaches the discomfort line (e.g., 39 degrees), then at that point the MCU may modify the stimulation mode to a comfort mode, with the stimulation intensity set to an intermediate gear and sound and vibration alerts based on reminder assembly, and in some embodiments may also be provided by the display screen simultaneous prompting a change in the stimulation strategy. If the temperature reaches the warning line (e.g., 41 degrees), then at this time the MCU may modify the stimulation mode to the comfort mode, the stimulation intensity is set to the lowest, and sound and vibration prompts are issued based on reminder assembly, and the user may also be prompted with the current temperature and the change of the stimulation strategy through display screen. Wherein, display screen may be realized based on a display module, as shown in FIG. 2, wherein the display module is electrically connected to the MCU to support display screen for effective display of relevant information.

In some embodiments, when the MCU, upon determining that temperature value exceeds a preset temperature threshold, may replace electrical stimulation intensity against electrode assembly, for example, by toning down the stimulation intensity, and at the same time, the user may be timely alerted via reminder assembly.

As a preferred embodiment of the present invention, the motion sickness prevention wristband provided by the present invention may also be provided with heating assembly (e.g., heater), as shown in FIG. 2, wherein heater is electrically connected to the MCU, and wherein the MCU determines that the air bag needs to be heated, the heating assembly is controlled to heat the air in the air bag.

Regarding the heating of air bag, it is mainly used here to simulate the effect of hot moxibustion, which further excites the median nerve through temperature elevation to enhance the stimulation effect. In addition to this, the temperature change induces sweating at the skin contact that is concave by the top of air bag, and the sweat possesses electrical conductivity, which can cause the dry electrode surface to be moistened by the salt solution, lowering the contact resistance, and thus significantly enhancing the effectiveness of the stimulation.

In some embodiments, the MCU can be informed of the temperature change in air bag by reading temperature value of temperature sensor, and control heater based on the temperature change, so that the temperature in air bag is stabilized or fluctuates in accordance with a curve, thereby achieving a stable and continuously effective electrical stimulation.

It is to be noted that the embodiment of the present invention may combine the MCU, electric air pump, air bag and pressure sensor to realize electrical stimulation. In the process of air bag regulation driven by electric air pump, pressure sensor may record the current skin pressure at electrode caused by wrist strap (herein, the wrist strap pressure is substituted for the wrist strap pressure), and the MCU calculates a sinusoidal-like curve of the optimal applied pressure against air bag based on the wrist strap pressure as shown in FIG. 3, and the pressure at curve In the case of the larger air pressure change indicated by the wave crest, applying electrical stimulation to electrode assembly can further enhance the effectiveness of electrical stimulation, which mainly takes into account that the larger air pressure change will enable wristband to better fit human skin, so that, in the case of the same stimulation energy, the stimulation effect is better at this time due to the fact that a more focused electrical stimulation can be performed.

Figure 3:
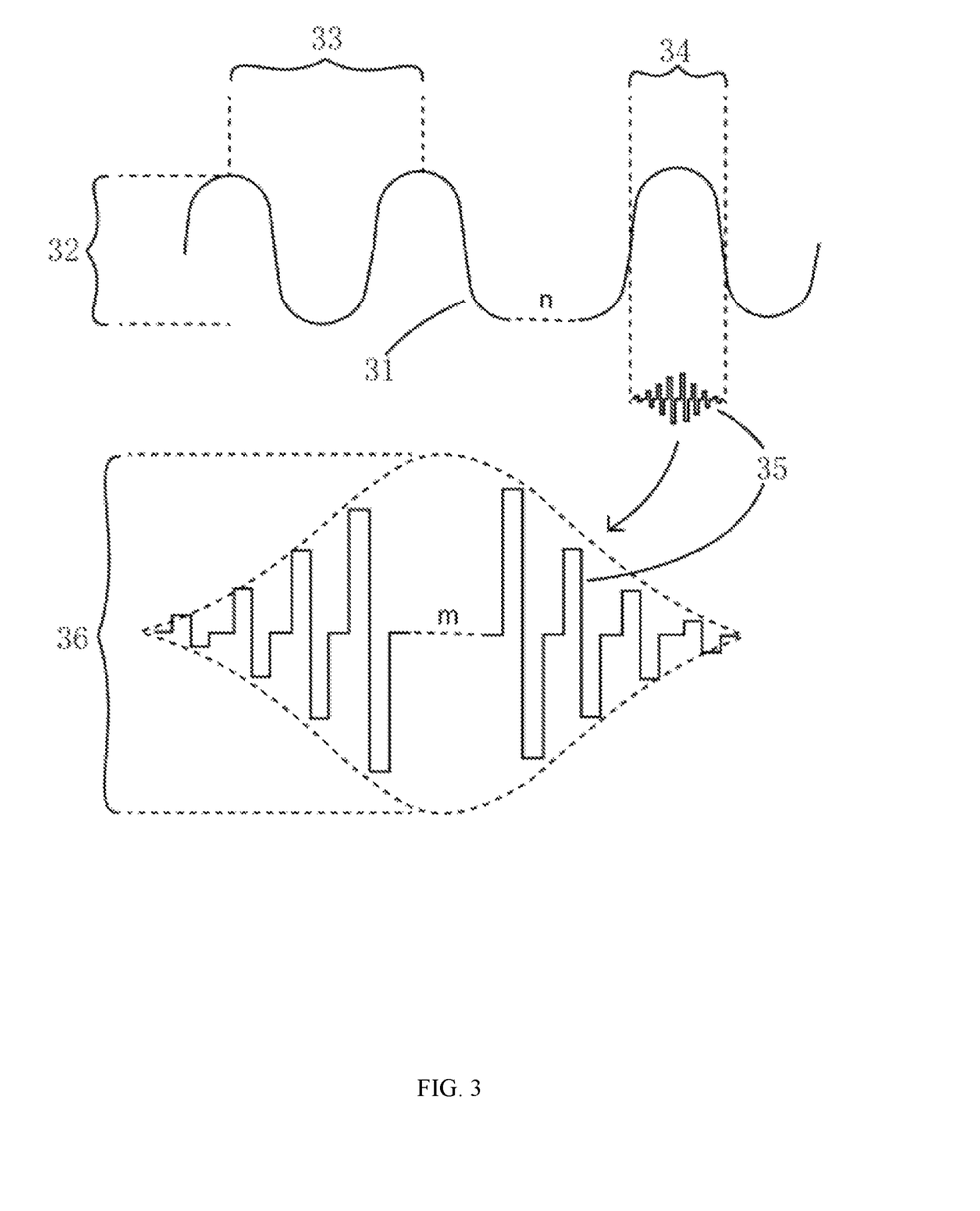
FIG. 3 is a schematic diagram of the method of air bag adjustment of the present invention.

Specifically, as illustrated in FIG. 3, curve 31 represents the curve of air pressure changes within air bag; 32 represents the amplitude between the peaks and the troughs of the air pressure curve of air bag, 33 represents the duration of one cycle of inflation and deflation of air bag, 34 represents the period of time during which electrical stimulation operates when the air pressure of air bag reaches half of the amplitude, 35 represents the waveform curve of electrical stimulation, and 36 represents the difference in the maximum amplitude of the waveform curve of electrical stimulation.

In addition, the dashed contour in the curve 35 in question represents the envelope of the oscillatory curve of curve 35 as it changes over time. Described herein is the fact that as the air pressure rises to the top, the magnitude difference of electrical stimulation also rises to the top, and as the air pressure falls the electrical stimulation magnitude falls.

As can be seen in FIG. 3 is that the detailed waveform of electrical stimulation herein is exemplified by a bidirectional square wave, for example, the bidirectional square wave is released through electrode piece fixed to air bag, this bidirectional square wave ensures that the area of the integral under the curve is 0, and there is no accumulation of charge due to the area covered by the positive and negative square waves canceling each other out to more nearly enhance the effect of the anti-vortex treatment.

In addition, m and n in FIG. 3 are used to indicate the number of repetitions of the pulse signal and the number of repetitions of the pressure signal, respectively, and herein is only a specific example, and the values of m and n are not specifically limited.

At the same time, the sinusoidal-like curve adjustment method adopted herein also allows the user to focus on the respiratory rate, and the discomfort caused by motion sickness can be alleviated to a certain extent by diverting attention.

As shown in FIG. 2, the motion sickness prevention wristband provided by the present invention may also be provided with a power supply module and a battery charging module to support the realization of the functions of each of the above modules, which will not be discussed herein.

Figure 4A:
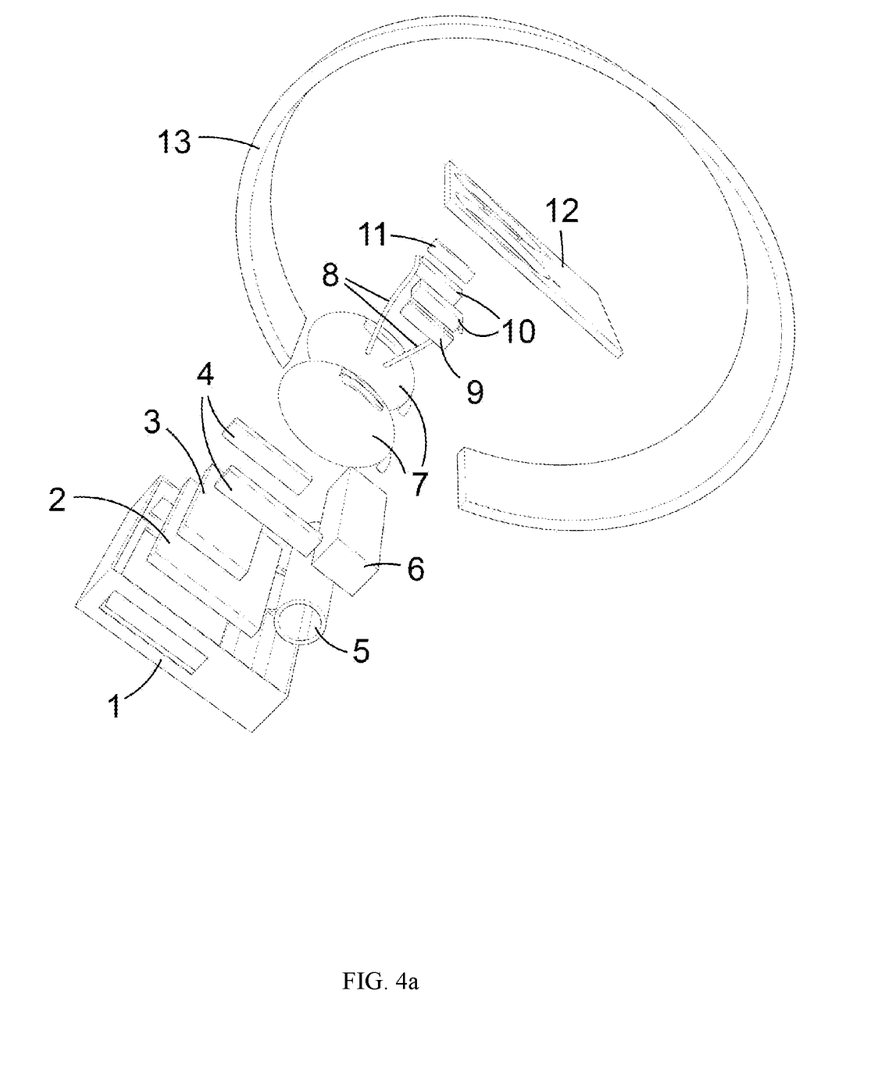
FIG. 4a is an isometric views of the motion sickness prevention wristband provided by the present invention.
Figure 4B:
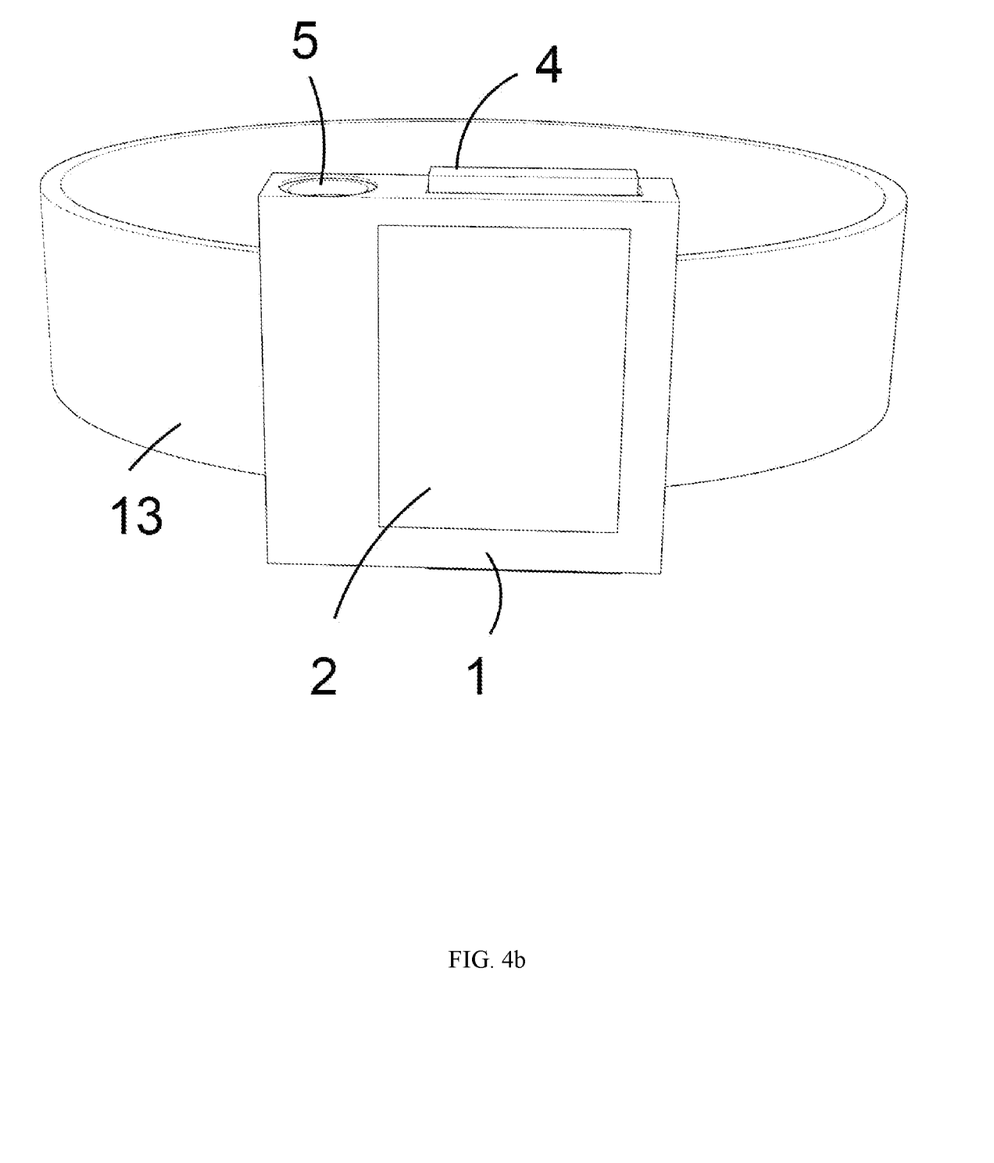
FIG. 4b is an isometric main views of the motion sickness prevention wristband provided by the present invention.
Figure 4C:
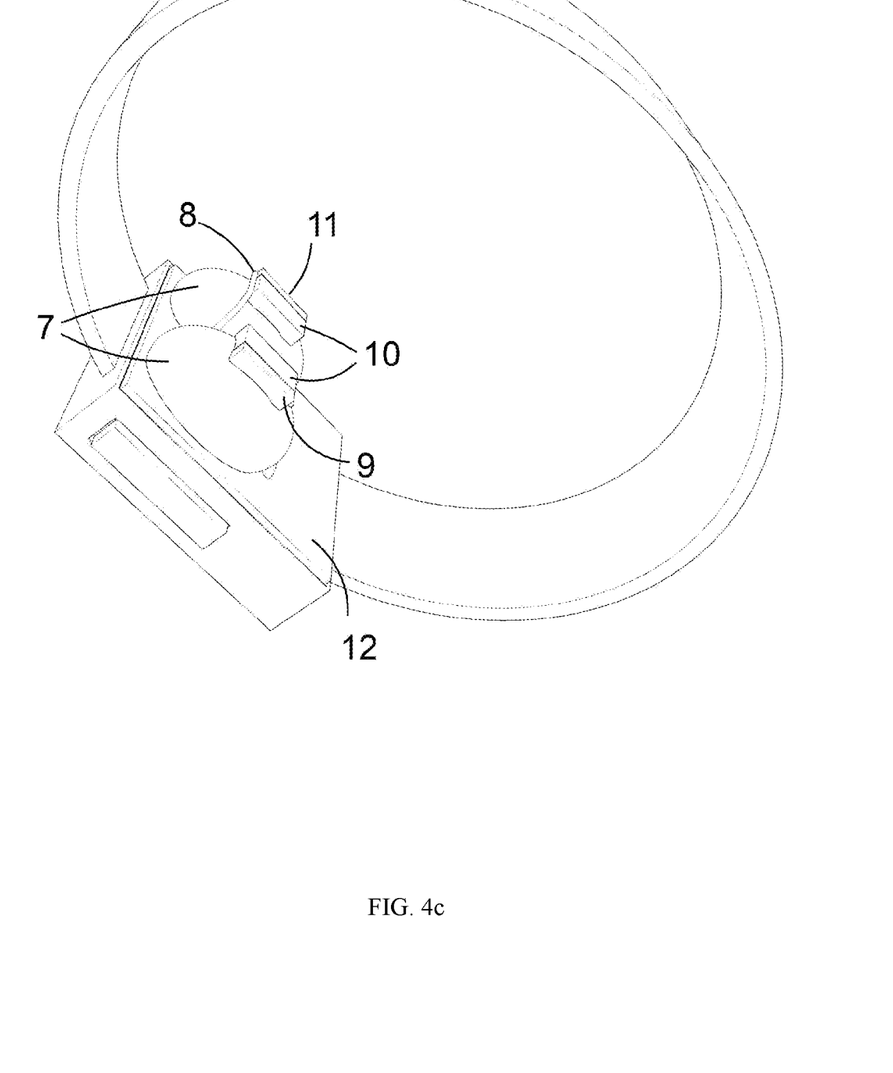
FIG. 4c is an isometric rear views of the motion sickness prevention wristband provided by the present invention.

In order to facilitate further understanding of the motion sickness prevention wristband in the embodiment of the present invention, the structure schematic diagrams shown in FIGS. 4a~4c are next combined for specific illustration.

The motion sickness prevention wristband in the embodiment of the present invention mainly includes a wristband disk portion and a wristband belt portion. As shown in FIG. 4a, the wristband disk portion may include top shell 1, bottom plate 12, and various components provided between top shell 1 and bottom plate 12, display screen 2, MCU 3, switch assembly 4, inflation port 5, air pump 6, air bag 7, connecting wire 8, temperature sensor 9, electrode piece 10, pressure sensor 11, and the like; in some embodiments, the wristband belt portion may be an wrist strap 13 that is mechanically adjusted to be elasticized or possessed of elasticity, for example It may be a nylon braided wrist strap 13 with slight elasticity and adjustable elasticity, which has excellent properties such as skin-friendly, hypoallergenic, breathable, etc.; in some other embodiments, the wristband belt may also be made of stainless steel, strong and durable wrist strap 13; in other embodiments, the wristband belt may also be made of a PVC material, which is chemically stable, and has excellent resistance to acids and alkalis.

To facilitate information display, first opening may be provided on top shell 1 to accommodate display screen 2, as shown in FIG. 4b, through which the user may be promptly reminded to tighten wearing wristband, in addition to other relevant prompts such as low power.

To facilitate a more direct electrical stimulation, second opening may be provided on bottom plate 12 to accommodate the air bag 7 control component, and in some embodiments, second opening may be used to accommodate air bag 7.

In the inflated state of air bag 7 shown in FIG. 4c, electrode piece 10 and human skin are able to fit further, and at the same time, connecting wire 8 is connected to pressure sensor 11, electrode piece 10, and temperature sensor 9, so that changes in the air pressure of air bag 7 do not affect the conduction of information and energy to connecting wire 8. In other embodiments (not shown in the figures), connecting wire 8 can also transmit signals and power supply to the MCU 3 in the MCU capped by bottom plate 12.

In some embodiments, air bag 7 is bonded and integrated with pressure sensor 11, electrode piece 10, and temperature sensor 9, and when air bag 7 is inflated and bulged, it tops up pressure sensor 11, electrode piece 10, and temperature sensor 9, with second opening provided on bottom plate 12 for the inflated air bag 7 to bulge and extend.

Considering that the polycarbonate (Polycarbonate, PC) material has excellent characteristics such as high strength and coefficient of elasticity, high impact strength, and a wide range of operating temperatures, top shell 1 can be made of PC material with openings for display screen 2, switch assembly 4, manual inflation port 5, etc. to pass through from the casing, and waterproofing of the openings and the connections with other parts by means of encapsulation adhesive, such as by polyurethane adhesive Encapsulation. In some embodiments, bottom plate 12, which is in contact with human skin, can be made of skin-friendly silicone or titanium and connected to other components by waterproof glue.

In this embodiment, display screen 2 is an OLED display with a length and width of 1.5 cm and 2.5 D. In some embodiments, the size of display screen 2 can be customized according to the user's usage needs and can have any desired size.

In this embodiment, the display is connected to the MCU 3 via a Flexible Printed Circuit (FPC), specifically, the MCU 3 is an ATMega328P-MU chip and its peripheral circuitry. In other embodiments, the MCU 3 may also be of other model configurations.

The button module (i.e., switch assembly 4) set up in this embodiment of the invention is electrically connected to the MCU 3 (see FIG. 2) for better implementation of wristband control. In this embodiment, switch assembly 4 may acquire a user-triggered switch signal and determine the switching state for wristband or electrical stimulation mode for electrode assembly by analyzing and processing by MCU 3.

In some embodiments, switch assembly 4 may control the switching state of wristband or control the switching of electrical stimulation mode of electrode assembly by a response of first switch, and may also control electrical stimulation intensity of electrode assembly by a response of second switch. In other embodiments, for example, a separate switch may be set up for electrical stimulation mode, and electrical stimulation mode may be integrated with electrical stimulation intensity in a single switch operation. In yet other embodiments, switch assembly 4 may have other configurations that are not specifically limited herein.

Whether first switch, second switch or other switches are provided on the side of top shell 1, for example, the switches may be inlaid through a plurality of openings provided on the side of top shell 1, the switches in question may have a shape such as a circle, an oval, a square, or any other desired geometrical shape, without specific limitation herein, and the switches in question may be a physical push button switch or a virtual touch switch, etc., also without specific limitation herein. The switch can be a physical button switch or a virtual touch switch, etc., and no specific restriction is made here.

Here we take one big button switch (corresponding to first switch) on one side of top shell 1 and two small buttons (corresponding to second switch) on the other side as an example. Each button is made of semi-transparent PC material of different colors. Low-power LED lamps can be integrated into the buttons. The buttons and lamps are connected to MCU 3, which transmits the pressing information to MCU 3, and MCU 3 drives the lamps.

In some embodiments, a large button switch on one side is long pressed to control the switch, long pressed for more than 2 seconds to turn the device on or off, the large button LED lights up during the power-on state, goes out during the power-off state, and blinks during the charging state, and the blinking frequency is matched to the battery's current power level. For example, the current battery power <30%, light 500 milliseconds off for 2 seconds; the current battery power is between 30% and 70% light 500 milliseconds off for 1 second; the current battery power >70%, light 500 milliseconds off for 500 milliseconds. The large button pressed for less than 2 seconds was regarded as a short press, and the short press could switch the stimulation mode. On the other side, two small button switches are used to adjust the stimulation intensity, and the surface of the buttons here can be engraved with high and low markings, and the LEDs inside the corresponding buttons will light up after the buttons are pressed, prompting the user that the buttons have been pressed.

Figure 5:
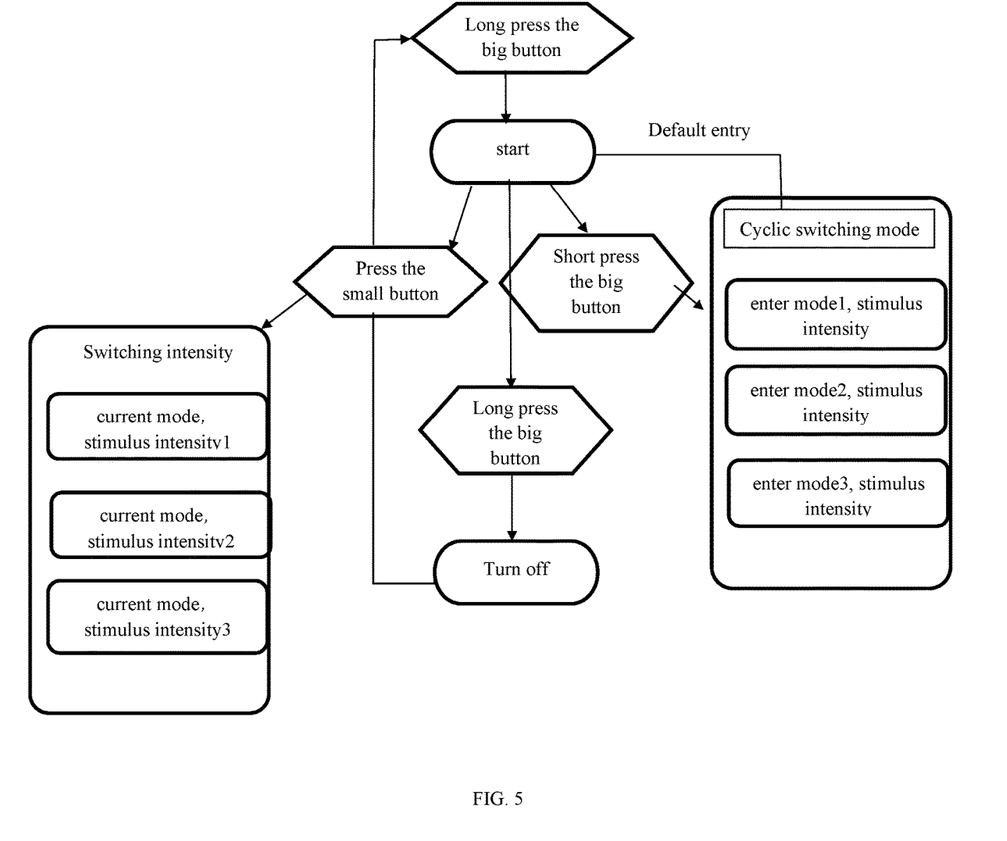
FIG. 5 is an isometric views of the method of switch adjustment provided by the present invention.

Based on the above switching control logic, the wristband state control and the electrode assembly stimulation mode/intensity control can be specifically realized in accordance with FIG. 5, for example, the three stimulation modes of the example can be determined, and the three stimulation intensities under the current mode can also be determined, and the specific switching process will not be discussed herein.

Figure 6:
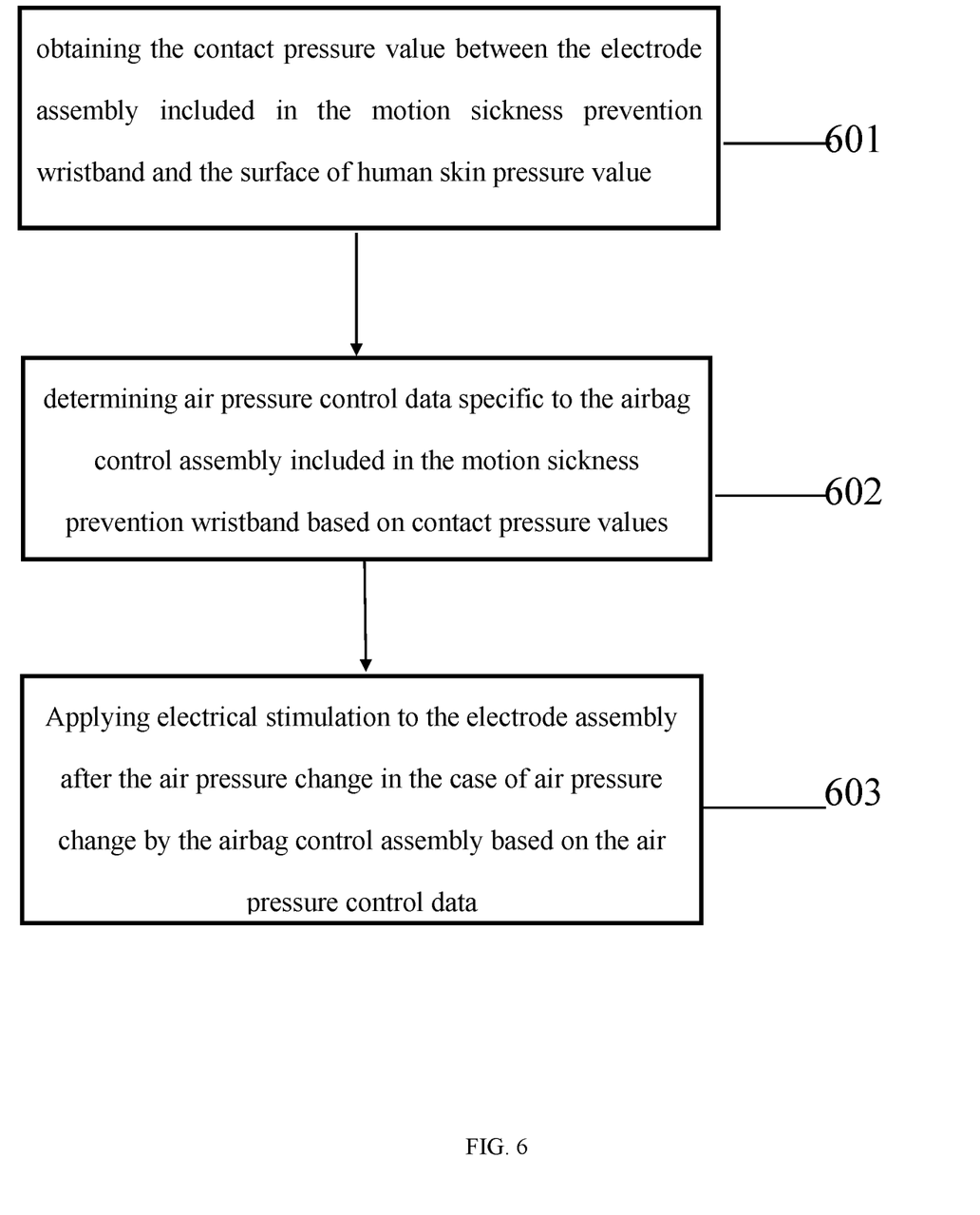
FIG. 6 is a flowchart of the control method of the motion sickness prevention wristband provided by the present invention.

Based on the motion sickness prevention wristband provided in the above embodiment, the present invention also provides a control method of the motion sickness prevention wristband, see FIG. 6 for a flowchart of the control method of the embodiment of the present invention, the method comprising:

601: obtaining contact pressure value between electrode assembly and human skin surfaces included in motion sickness prevention wristband;

602: determining air pressure control data based on contact pressure value against air bag control assembly included in motion sickness prevention wristband;

603: applying electrical stimulation to the electrode assembly after the air pressure change in case the air bag control assembly undergoes air pressure change based on air pressure control data.

Using the control method of motion sickness prevention wristband described above, the contact pressure value between the electrode assembly included in motion sickness prevention wristband and the surface of human skin is obtained; the air pressure control data targeting the air bag control assembly included in motion sickness prevention wristband is determined based on the contact pressure value; and the electrical stimulation is applied to the electrode assembly after the air pressure change in case the air bag control assembly undergoes an air pressure change based on the air pressure control data. In the present invention, as the air pressure change makes the electrode assembly better tightened to the skin, the electrical stimulation performed at this time can maintain the stabilized contact resistance and ensure the effectiveness of electrical stimulation, thereby significantly enhancing the anti-motion sickness effect.

In a possible embodiment, applying electrical stimulation to electrode assembly after the air pressure change comprises:

applying electrical stimulation to electrode assembly after determining that a predetermined electrical stimulation condition is reached based on the air pressure change.

In a possible embodiment, further comprising:

In the case where it is determined that the updated contact pressure value between the electrode assembly and the surface of the human skin after the air pressure change is less than the predetermined pressure value, generating a reminder signal for alerting the user to tighten the wearing of the wristband;

Performing a reminder operation for the user to tighten the wearing of the wristband based on the reminder signal.

The control logic in question is specifically described in relation to motion sickness prevention wristband above and will not be repeated herein.

With respect to the method flowchart of an embodiment of the present invention, certain operations are depicted as different steps performed in a certain order. Such a flowchart is illustrative rather than restrictive. Certain steps described herein may be grouped together and performed in a single operation, certain steps may be split into a plurality of sub-steps, and certain steps may be performed in a different order than shown herein. The steps illustrated in the flowchart may be implemented in any manner by any circuit structure and/or tangible mechanism (e.g., software, hardware (e.g., processor or chip-implemented logic functions), etc., running on a computer device, and/or any combination thereof).

It will be understood by those skilled in the art that, in specific embodiments of the above method, the order in which the steps are written does not imply any limitation of the implementation process by means of a strict order of execution, and that the specific order of execution of the steps should be determined in terms of their functionality and possible intrinsic logic.

Based on the same inventive concept, the embodiment of the present invention also provides a control device of motion sickness prevention wristband corresponding to the control method of motion sickness prevention wristband. Since the device in the embodiment of the present invention solves the problem in a similar way as the principle of the above-described control method of motion sickness prevention wristband in the embodiment of the present invention, the implementation of the device can be referred to the implementation of the method, and repetitions will not be repeated.

Figure 7:
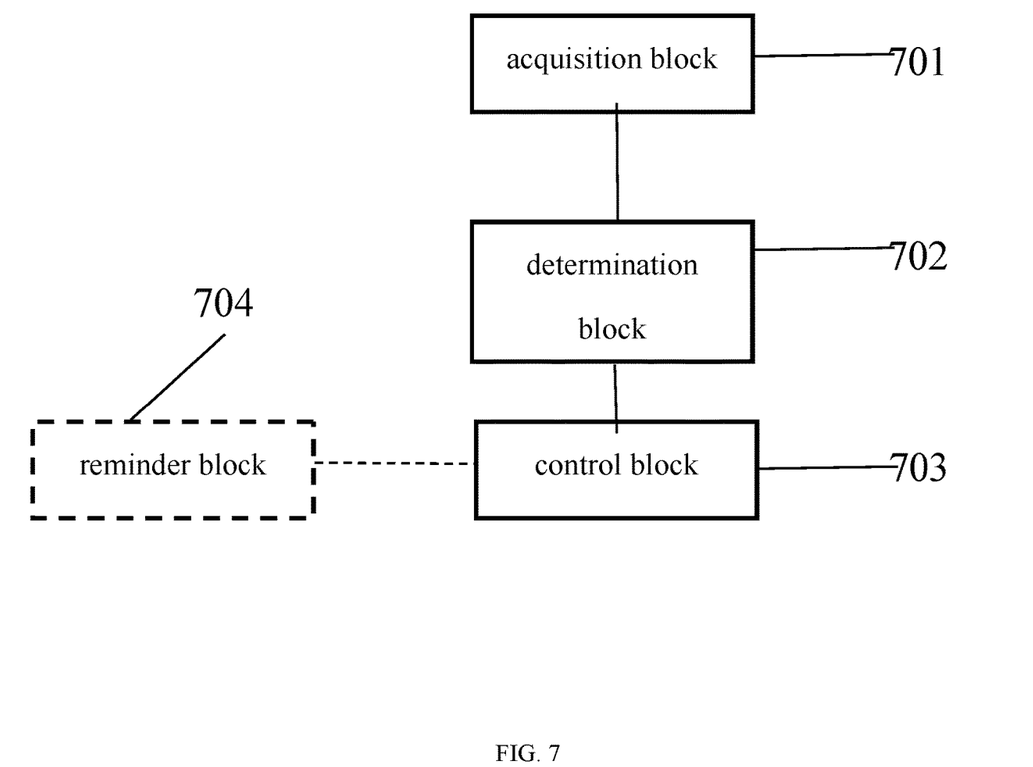
FIG. 7 is a schematic diagram of the control device of the motion sickness prevention wristband provided by the present invention.

Referring to FIG. 7, a schematic diagram of a control device for motion sickness prevention wristband provided by the present invention is shown, the device comprising: an acquisition block 701, a determination block 702, and a control block 703; wherein acquisition block 701, for obtaining contact pressure value between electrode assembly and human skin surfaces included in motion sickness prevention wristband;

determination block 702, for determining air pressure control data against air bag control assembly included in motion sickness prevention wristband based on contact pressure value;

control block 703, for applying electrical stimulation to electrode assembly after the air pressure change in case air bag control assembly undergoes the air pressure change based on air pressure control data.

In a possible embodiment, control block 703, for applying electrical stimulation to electrode assembly after the air pressure change according to the following steps:

Applying electrical stimulation to electrode assembly after determining that a predetermined electrical stimulation condition has been reached based on the air pressure change.

In a possible embodiment, it further comprises:

reminder block 704, for generating reminder signal for reminding the user to tighten wearing wristband in case it is determined that the updated contact pressure value between electrode assembly and the surface of human skin after the change in air pressure is less than the predetermined pressure value; and performing a reminder operation of tightening wearing wristband to the user based on reminder signal.

It should be appreciated by those skilled in the art that embodiments of the present invention may be provided as a method, an apparatus (device or system), or a computer-readable storage medium. Thus, the present invention may take the form of a fully hardware implementation, a fully software implementation, or an implementation that combines software and hardware aspects. Further, the present invention may take the form of a computer-readable storage medium implemented on one or more computer-usable storage media (including, but not limited to, disk memory, CD-ROM, optical memory, and the like) that contain computer-usable program code therein.

The present invention is described with reference to flowcharts and/or block diagrams of methods, apparatus (devices or systems), and computer-readable storage media according to embodiments of the present invention. It is to be understood that each of the processes and/or boxes in the flowchart and/or block diagram, and combinations of the processes and/or boxes in the flowchart and/or block diagram, may be implemented by computer program instructions. These computer program instructions may be provided to a processor of a general-purpose computer, a special-purpose computer, an embedded processor, or other programmable data-processing device to produce a machine such that the instructions executed by the processor of the computer or other programmable data-processing device produce a device for carrying out the functions specified in the one process or multiple processes of the flowchart and/or the one box or multiple boxes of the box diagram.

These computer program instructions may also be stored in computer-readable memory capable of directing the computer or other programmable data processing device to operate in a particular manner such that the instructions stored in the computer-readable memory produce an article of manufacture comprising an instruction device that implements the function specified in the flowchart one process or a plurality of processes and/or the box diagram one box or a plurality of boxes.

These computer program instructions may also be loaded onto a computer or other programmable data processing device such that a series of operational steps are performed on the computer or other programmable device to produce computer-implemented processing, such that the instructions executed on the computer or other programmable device provide steps for implementing the functionality specified in the flowchart one process or a plurality of processes and/or the box diagram one box or a plurality of boxes.

In an exemplary configuration, the computing device includes one or more processors (CPUs), an input/output interface, a network interface, and memory.

Memory may include forms of non-permanent memory, random access memory (RAM) and/or non-volatile memory in computer-readable media, such as read-only memory (ROM) or flash memory (flash RAM). Memory is an example of a computer-readable medium.

Computer-readable media includes permanent and non-permanent, removable and non-removable media may be implemented by any method or technique for information storage. The information may be computer-readable instructions, data structures, modules of a program, or other data. Examples of storage media for computers include, but are not limited to, phase-change memory (PRAM), static random-access memory (SRAM), dynamic random-access memory (DRAM), other types of random-access memory (RAM), read-only memory (ROM), electrically erasable programmable read-only memory (EEPROM), flash memory or other memory technologies, read-only CD-ROMs, and read-only memory. Read Only Memory (CD-ROM), Digital Versatile Disc (DVD) or other optical storage, magnetic cartridge tape, magnetic tape disk storage or other magnetic storage device, or any other non-transfer medium that can be used to store information that can be accessed by a computing device. Furthermore, although the operations of the method of the present invention are described in the accompanying drawings in a particular order, it is not required or implied that the operations must be performed in that particular order or that all of the operations shown must be performed in order to achieve the desired results. Additionally, or alternatively, certain steps may be omitted, a plurality of steps may be combined to be performed as a single step, and/or a single step may be broken down to be performed as a plurality of steps.

The technical means disclosed in the scheme of the present invention are not limited to the technical means disclosed in the above embodiments, but also include the technical scheme composed of any combination of the above technical features. It should be pointed out that for those skilled in the art, several improvements and embellishments can be made without departing from the principle of the present invention, and these improvements and embellishments are also regarded as the protection scope of the present invention.

The invention has now been described in detail for the purposes of clarity and understanding. However, those skilled in the art will appreciate that certain changes and modifications may be practiced within the scope of the appended claims.

What is claimed is:

1. A motion sickness prevention wristband comprising a wristband body, a microcontroller unit (MCU), a pressure sensor, an electrode assembly and an air bag control assembly,
   wherein said pressure sensor, said electrode assembly, and said air bag control assembly are electrically connected to said MCU, said air bag control assembly being offset from said electrode assembly;
   said pressure sensor is to configured to obtain a contact pressure value between said electrode assembly and a surface of human skin and to transmit said contact pressure value to said MCU;
   said MCU determining air pressure control data of the air bag control assembly based on the contact pressure value and transmitting the air pressure control data to said air bag control assembly;
   the air bag control assembly making an air pressure change based on said air pressure control data to control the MCU to apply electrical stimulation to the surface of human skin via said electrode assembly after the air pressure changes, wherein said air bag control assembly comprises a manual inflation and deflation unit and an air bag; wherein said manual inflation and deflation unit comprises an inflation port, a one-way air valve, and a one-key deflation button;
   wherein the inflation port is to configured to assist in manually pumping a gas into the air bag so that said one-way air valve deposits secures the pumped gas within said air bag; and wherein said one-key deflation button is to configured to open said one-way air valve for deflation of said air bag.

2. A method of controlling a motion sickness prevention wristband, the method comprising:
   providing a motion sickness prevention wristband, said motion sickness prevention wristband comprising a wristband body, a microcontroller unit (MCU), a pressure sensor, an electrode assembly, and an air bag control assembly, the pressure sensor, said electrode assembly, and said air bag control assembly being electrically coupled to said MCU, the air bag control assembly being pressed against said electrode assembly; said pressure sensor being configured to obtain a contact pressure value between said electrode assembly and a surface of human skin and transmit said contact pressure value to said MCU; and said MCU configured to determine air pressure control data based on said contact pressure value and transmit said air pressure control data to said air bag control assembly for controlling an air pressure of an air bag; said air bag control assembly undergoing an air pressure change based on said air pressure control data and said MCU applying electrical stimulation to said electrode assembly after the air pressure change;
   said method further comprising:
   obtaining the contact pressure value between the electrode assembly of said motion sickness prevention wristband and the surface of human skin;
   determining the air pressure control data of said air bag control assembly of said motion sickness prevention wristband based on said contact pressure value; and
   applying the electrical stimulation to said electrode assembly after the air pressure change;
   wherein the electrical stimulation is further applied to the surface of human skin by said electrode assembly.

3. The method of controlling a motion sickness prevention wristband according to claim 2, wherein said applying the electrical stimulation to said electrode assembly after the air pressure change comprises:
applying the electrical stimulation to said electrode assembly after determining that a predetermined electrical stimulation condition has been reached based on the air pressure change.

4. The method of controlling a motion sickness prevention wristband according to claim 3, further comprising:
generating a reminder signal for reminding a user to tighten a wearing of the wristband in case said MCU determines that an updated contact pressure value between said electrode assembly and the surface of the human skin after the air pressure change is less than a preset pressure value; and
performing a reminder operation for the user to tighten the wearing of the wristband based on said reminder signal.

5. The method of controlling a motion sickness prevention wristband according to claim 2, further comprising:
generating a reminder signal for reminding a user to tighten a wearing of the wristband in case said MCU determines that an updated contact pressure value between said electrode assembly and the surface of the human skin after the air pressure change is less than a preset pressure value; and
performing a reminder operation for the user to tighten the wearing of the wristband based on said reminder signal.

6. The method of controlling a motion sickness prevention wristband according to claim 2, wherein said air bag control assembly comprises an electric air pump and an air bag; said electric air pump being electrically connected to said MCU; said electric air pump for determining an airbag volume according to said air pressure control data; wherein said airbag is inflated or deflated by said electric air pump according to said air pressure control data.

7. The method of controlling a motion sickness prevention wristband according to claim 6, wherein said air bag is provided with an air pressure sensor inside said air bag; wherein said air pressure sensor is electrically connected to said MCU; said air pressure sensor for detecting an air pressure inside said air bag and transmitting said air pressure to said MCU; and said MCU for determining said air pressure control data for controlling said electric air pump, based on said air pressure.

8. The method of controlling a motion sickness prevention wristband according to claim 7, wherein said motion sickness prevention wristband further comprises a temperature sensor; said temperature sensor being electrically connected to said MCU; said temperature sensor being configured to detect a temperature value of a contacting surface of said electrode assembly contacting the surface of human skin and to transmit said temperature value to said MCU; said MCU being configured to determine, based on said temperature value, a temperature adjustment strategy, and/or an electrical stimulation strategy.

9. The method of controlling a motion sickness prevention wristband according to claim 8, wherein said motion sickness prevention wristband further comprises a heating assembly; said heating assembly being electrically connected to said MCU; said MCU being further configured to control said heating assembly to heat a gas within said air bag when said MCU determines that said air bag needs to be heated according to said temperature value.

10. The method of controlling a motion sickness prevention wristband according to claim 8, wherein said motion sickness prevention wristband further comprises a reminder assembly; said reminder assembly being electrically connected to said MCU; said MCU being further configured to change an electrical stimulation intensity of said electrode assembly when the temperature value exceeds a preset temperature threshold; said reminder assembly being used for alerting based on a change of the electrical stimulation intensity.

11. The method of controlling a motion sickness prevention wristband according to claim 7, wherein said MCU is further configured to:
generate a reminder signal for reminding a user in case said MCU determines that an updated contact pressure value between said electrode assembly and the surface of human skin after the air pressure change is less than a predetermined pressure value.

12. The method of controlling a motion sickness prevention wristband according to claim 11, wherein said motion sickness prevention wristband further comprises a display screen; and said display screen is configured to display a reminder information of tightening the wearing of the wristband to the user based on said reminder signal.

13. The method of controlling a motion sickness prevention wristband according to claim 12, wherein said motion sickness prevention wristband further comprises a top shell provided with a first opening, and a bottom plate provided with a second opening; wherein the top shell is capped by the bottom plate; the first opening is configured to accommodate said display screen; and said second opening is used to accommodate said air bag control assembly.

14. The method of controlling a motion sickness prevention wristband according to claim 7, wherein said motion sickness prevention wristband further comprises a switch assembly; the switch assembly being electrically connected to said MCU; said switch assembly for obtaining a switch signal triggered by a user and transmitting said switch signal to said MCU; and said MCU for determining, based on a duration of actuation of said switch signal, a switch state of the wristband, or an electrical stimulation mode and an electrical stimulation intensity of said electrode assembly.

15. The method of controlling a motion sickness prevention wristband according to claim 14, wherein said switch assembly comprises a first switch and a second switch; the first switch being configured to cause said MCU to control the wristband to be switched on or off in response to a switch signal that exceeds a preset time or, alternatively, to cause said MCU to switch the electrical stimulation mode directed to said electrode assembly in response to said switch signal being less than the preset time; and said second switch being configured to adjust the electrical stimulation intensity under a switched electrical stimulation mode.

16. The method of controlling a motion sickness prevention wristband according to claim 7, wherein said MCU is further configured to: apply the electrical stimulation to said electrode assembly when a preset electrical stimulation condition is determined to have been reached based on the air pressure change.

17. The method of controlling a motion sickness prevention wristband according to claim 6, wherein said motion sickness prevention wristband further comprises a temperature sensor; said temperature sensor being electrically connected to said MCU; said temperature sensor for detecting a temperature value of a contacting surface of said electrode assembly contacting the surface of human skin and transmitting said temperature value to said MCU; said MCU for determining, based on said temperature value, a temperature adjustment strategy and/or an electrical stimulation strategy.

18. The method of controlling a motion sickness prevention wristband according to claim 6, wherein said electrode assembly comprises two electrode pieces, the motion sickness prevention wristband comprising two air bags, each of said electrode pieces being arranged on one of said two air bags.

19. The method of controlling a motion sickness prevention wristband according to claim 2, wherein an inflation port is configured to assist in manually pumping a gas into the air bag so that an air valve secures the pumped gas within said air bag; and wherein a one-key deflation button is configured to open said one way air valve for deflation of said air bag.

\* \* \* \* \*